United States Patent
Van Der Mark et al.

(10) Patent No.: US 11,422,308 B2
(45) Date of Patent: Aug. 23, 2022

(54) TIP REFLECTION REDUCTION FOR SHAPE-SENSING OPTICAL FIBER

(75) Inventors: Martinus Bernardus Van Der Mark, Best (NL); Raymond Chan, San Diego, CA (US); Robert Manzke, Eindhoven (NL); Gert Wim 'T Hooft, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1499 days.

(21) Appl. No.: 13/981,933

(22) PCT Filed: Jan. 24, 2012

(86) PCT No.: PCT/IB2012/050328
§ 371 (c)(1),
(2), (4) Date: Nov. 15, 2013

(87) PCT Pub. No.: WO2012/101579
PCT Pub. Date: Aug. 2, 2012

(65) Prior Publication Data
US 2014/0073912 A1 Mar. 13, 2014

Related U.S. Application Data

(60) Provisional application No. 61/470,058, filed on Mar. 31, 2011, provisional application No. 61/437,039, filed on Jan. 28, 2011.

(51) Int. Cl.
*G02B 6/24* (2006.01)
*A61B 5/06* (2006.01)
*G02B 6/26* (2006.01)
*A61B 1/00* (2006.01)
*A61B 34/20* (2016.01)

(52) U.S. Cl.
CPC .............. *G02B 6/24* (2013.01); *A61B 1/0017* (2013.01); *A61B 5/065* (2013.01); *A61B 34/20* (2016.02); *G02B 6/243* (2013.01); *G02B 6/262* (2013.01); *A61B 2034/2061* (2016.02); *A61B 2562/0266* (2013.01)

(58) Field of Classification Search
CPC .................... G02B 6/26–268; G02B 6/24–243
See application file for complete search history.

(56) References Cited

U.S. PATENT DOCUMENTS

| | | | |
|---|---|---|---|
| 5,058,983 A | 10/1991 | Corke et al. | |
| 5,191,467 A * | 3/1993 | Kapany | G02B 6/2746 359/337 |
| 5,263,103 A | 11/1993 | Kosinski | |

(Continued)

FOREIGN PATENT DOCUMENTS

| | | |
|---|---|---|
| CN | 101788478 A | 7/2010 |
| EP | 1587184 A1 | 10/2005 |

(Continued)

*Primary Examiner* — Serkan Akar (57) ABSTRACT

A reflection reduction device includes an optical fiber (104) configured for optical sensing and having an end portion. A tip portion (102) is coupled to the end portion. The tip portion includes a length dimension (d) and is index matched to the optical fiber. The tip portion is further configured to include an absorption length to absorb and scatter light within the length dimension, and a surface (S) opposite the end portion is configured to reduce back reflections.

19 Claims, 3 Drawing Sheets

(56) References Cited

U.S. PATENT DOCUMENTS

| | | | |
|---|---|---|---|
| 5,342,355 A | 8/1994 | Long | |
| 5,822,478 A * | 10/1998 | Kim | G02B 6/243 |
| | | | 385/33 |
| 5,859,944 A * | 1/1999 | Inoue | G02B 6/021 |
| | | | 385/73 |
| 6,115,524 A | 9/2000 | Burke et al. | |
| 6,168,319 B1 * | 1/2001 | Francis | G02B 6/2937 |
| | | | 385/55 |
| 6,424,765 B1 * | 7/2002 | Harker | G02B 6/262 |
| | | | 385/31 |
| 6,804,281 B1 * | 10/2004 | Walpole | H01S 5/10 |
| | | | 372/45.01 |
| 7,356,225 B2 | 4/2008 | Loebel | |
| 8,488,924 B2 * | 7/2013 | Lee | G02B 6/421 |
| | | | 385/31 |
| 10,126,502 B2 * | 11/2018 | Ishikawa | G02B 6/1228 |
| 2002/0041733 A1 * | 4/2002 | Mihailov | G02B 6/02138 |
| | | | 385/37 |
| 2004/0047535 A1 | 3/2004 | Ukrainczyk | |
| 2006/0018596 A1 | 1/2006 | Loebel | |
| 2006/0188212 A1 | 8/2006 | Oron et al. | |
| 2007/0127870 A1 * | 6/2007 | Oron | A61B 18/28 |
| | | | 385/38 |
| 2007/0156019 A1 * | 7/2007 | Larkin | B25J 19/025 |
| | | | 600/104 |
| 2008/0015560 A1 * | 1/2008 | Gowda | A61N 5/062 |
| | | | 606/15 |
| 2008/0212082 A1 * | 9/2008 | Froggatt | G01D 5/35316 |
| | | | 356/73.1 |
| 2009/0306637 A1 | 12/2009 | Esch et al. | |
| 2010/0104244 A1 * | 4/2010 | Grinderslev | G02B 6/32 |
| | | | 385/74 |
| 2011/0122366 A1 * | 5/2011 | Smith | G02B 6/262 |
| | | | 351/221 |
| 2011/0184244 A1 * | 7/2011 | Kagaya | A61B 1/00128 |
| | | | 600/182 |
| 2011/0207237 A1 * | 8/2011 | Sai | G01N 21/554 |
| | | | 436/518 |
| 2012/0057841 A1 * | 3/2012 | Wysocki | G02B 6/243 |
| | | | 385/139 |

FOREIGN PATENT DOCUMENTS

| | | |
|---|---|---|
| JP | 2007279443 A | 10/2007 |
| JP | 2008272301 A | 11/2008 |
| JP | 2008272302 A | 11/2008 |
| JP | 2010107239 A | 5/2010 |
| WO | WO2005036210 | 4/2005 |

* cited by examiner

TIP REFLECTION REDUCTION FOR SHAPE-SENSING OPTICAL FIBER

CROSS-REFERENCE TO PRIOR APPLICATIONS

This application is the U.S. National Phase application under 35 U.S.C. § 371 of International Application Serial No. PCT/IB2012/050328, filed on Jan. 24, 2012, which claims the benefits of U.S. Applications Ser. Nos. 61/470,058, filed on Mar. 31, 2011 and 61/437,039, filed on Jan. 28, 2011. These applications are hereby incorporated by reference herein.

This disclosure relates to medical instruments and more particularly to shape sensing optical fibers in medical applications that include reduced tip reflections.

The ability to accurately sense the tip and shape of a medical instrument or device plays a key role in interventional guidance. A technology based on optical shape sensing for localization is known. However, the manner of attachment of the fiber to an instrument plays a role in how tracking and/or shape sensing is performed. For example, if an optical fiber is attached along the length of a catheter and terminates abruptly at the tip of the distal end, backscattering due to Fresnel reflections at the tip can interfere with the desired optical signal.

Coupling the tip of the fiber with index matching gel to dissipate light out into the surrounding tissue medium can help to reduce Fresnel reflection effects at the fiber tip. However, while this approach is workable in a laboratory, it can complicate manufacturing of medical grade products.

Shape sensing based on fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

When an optical fiber is attached along the length of a catheter, it terminates abruptly at the tip of the distal end. In this configuration, backscattering due to reflections at the tip interface can interfere with a desired optical grating or backscattering signal. In practice, this results in a signal on the detector with extra noise and compromises the dynamic range of the detector, amplifier and sampling accuracy of the system. In particular, for a certain level of reflection the phase noise of the laser may become limiting.

Coupling the tip of the fiber with index matching gel to dissipate light out into the surrounding tissue medium can reduce back-reflection effects. As mentioned, this approach can complicate manufacturing of medical grade products. Furthermore, it is only a partial solution since the optimal refractive index of the coupling gel depends on the tissue that the instrument operates within (e.g., air versus blood).

Fiber loops at the tip of the catheter have been employed so that the distal fiber end is far away from the catheter tip. The fiber loops can even be in the laboratory instrument outside the patient. Then, the end portion can be dealt with appropriately, since the surrounding environment is known and there is space to put the distal end in any size, shape or form of matching medium. The looping solution has two practical challenges. First, the loop itself will have to be very tight, but nonetheless should keep the same single-mode character of the whole fiber waveguide. Second, effectively, the catheter has to be made with twice the amount of fiber for a return path.

In accordance with the present principles, a tip configuration for a medical instrument is provided which provides light absorption and index matching. The tip configuration is compact and may be biocompatible.

A reflection reduction device includes an optical fiber configured for optical sensing and having an end portion. A tip portion is coupled to the end portion. The tip portion includes a length dimension and is index matched to the optical fiber. The tip portion is further configured to include an absorption length to absorb and scatter light within the length dimension, and a surface (S) opposite the end portion configured to reduce back reflections.

A shape sensing system includes a shape sensing enabled medical device having at least one optical fiber. A console is configured to receive optical signals from the at least one optical fiber and interpret the optical signals to determine a shape of the medical device. A tip portion is coupled to a distal end portion of the at least one optical fiber, the tip portion including a length dimension and being indexed matched to the optical fiber. The tip portion is further configured to include an absorption length to absorb and scatter light within the length dimension.

A method for end-reflection reduction of an optical shape-sensing fiber includes providing a tip portion; connecting the tip portion to an end portion of an optical fiber configured for optical shape-sensing, the tip portion being indexed matched to the optical fiber; and adjusting the absorption properties of the tip portion using back reflections as feedback to provide an absorption length for light traveling in the optical fiber to reduce the back reflections.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, a tip configuration for a medical instrument or other fiber optic system is provided which provides light absorption and index matching. The tip configuration is compact and is preferably formed in a manner that permits biocompatible use in vivo (e.g., glass doped with a strong absorber, colloidal polymer nanospheres or mineral impurities which absorb light, in combination with termination tip coating which is protective and biocompatible, a polymer sheath such as PEBAX, PTFE, silicone, etc.). The ability to accurately sense the tip and shape of a medical instrument or device plays a role in interventional guidance to make use of fiber optic shape sensing and localization. The tip of an instrument in accordance with the present principles incorporates fiber optic shape sensing and localization, has light absorbing properties and index-matches the optical fiber.

In one embodiment, a tip configuration which has both light absorbing and index matching properties provides low light scattering and is small enough to avoid compromising shape sensing even toward the end of the medical instrument (e.g., a guide wire or catheter) that incorporates fiber optic shape sensing. Material deposited at the tip has absorption that is sufficiently large at an interrogation wavelength, and both its refractive index and its absorption are set such that an index mismatch is sufficiently low, in particular at the temperature of use, e.g., 37° C. for medical practice. An interface between the fiber and absorber tip may be slanted to minimize reflection in the case where imperfect refractive index matching occurs. An optical shape (S) and finish of the distal end of the tip portion determine the direction of back reflected light.

It also should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
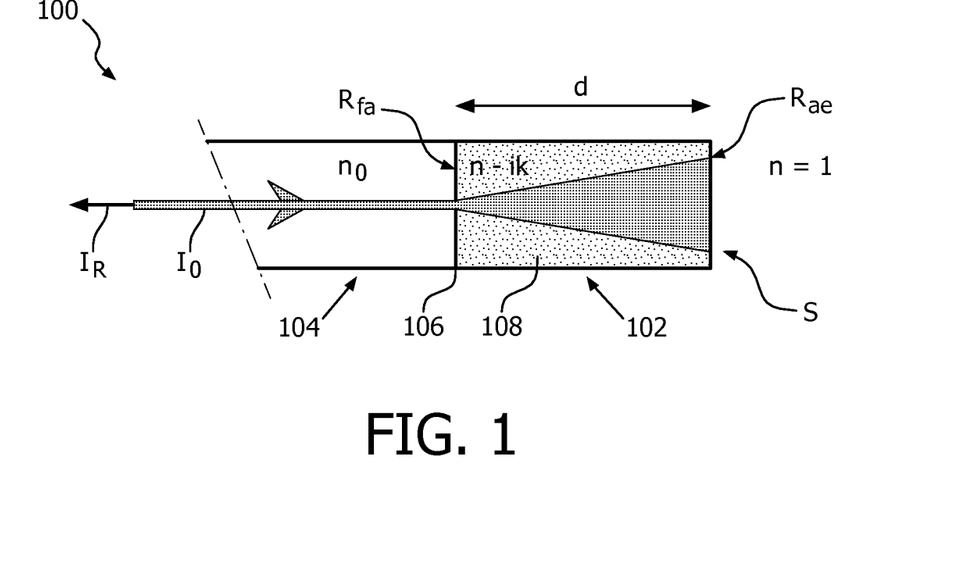
FIG. 1 is a tip configuration for providing a beneficial end condition to an optical fiber in accordance with the present principles.

Referring now to the drawings in which like numerals represent the same or similar elements and initially to FIG. 1, a tip configuration 100 includes a tip portion 102 connected to an optical fiber 104. The optical fiber 104 may include a distal end portion of a medical device having shape-sensing capabilities. The medical device may include, e.g., a catheter, a guide wire, an endoscope, a probe, a robot, an electrode, a filter device, a balloon device, or other medical component, etc. The tip portion 102 is formed from a material that is both light absorbing and index matching with fiber 104 and surrounding materials. In one embodiment, the tip portion 102 is low light scattering. Further, it is preferable that the tip portion 102 be small so that it does not compromise shape sensing or miniaturization of medical instrument design, and shape sensing may be provided down to the end of the medical instrument that the shape sensing fiber 104 is part of.

The tip portion 102 includes a light absorption property that is sufficiently large at an interrogation wavelength employed for shape sensing. In this way, the light traveling down the fiber 104 is not reflected back and/or is attenuated to prevent negative effects in shape-sensing. In one embodiment, both a refractive index and absorption of the tip portion 102 provide a low index mismatch between the tip portion 102 and the fiber 104, in particular, at a temperature of usage, e.g., 37° C. for medical practice. The tip portion 102 includes light absorbing/scattering materials 108 (e.g., dopants and/or particulates) to reduce back reflections.

The tip portion 102 may include a glue or other adhesive, a composite containing an absorbent (e.g., dye, pigment, colloidal or other particulate doping material), an antireflection coated volume or semiconductor, a fiber segment spliced onto the end portion of the fiber, a ferrule or other mechanical connection or other material which can provide the desired properties. The tip portion 102 is preferably made of materials that permit use in biological structures or is sufficiently encased in a biocompatible material. Such materials may include biocompatible polymers, such as, e.g., PET, PTFE, PEBAX, silicone, MMA, or other similar materials.

For example, the absorbent (108) may include a metal, where at a plasmon frequency, the material's relative permittivity, $\varepsilon_r$, is approximately 2 ($\varepsilon_r = n^2 - k^2$, $\varepsilon_i = 2nk$), where n and k are the real and imaginary parts of the index of refraction of the material. The real part of the refractive index n indicates the phase speed and the imaginary part k indicates the amount of absorption loss when the electromagnetic wave propagates through the material. k is called the extinction coefficient. The absorbent material (108) in the tip portion 102 may include carbon based materials, such as, graphite, nanotubes, buckyballs, etc., a metal complex (e.g., Ruthenium based) or a photonic crystalline nanostructure. The absorbent (108) may include metal particles, cations, anions, or molecules that absorb light of the wavelength desired dispersed in a matrix (e.g., of glass or other material).

In other embodiments, the absorbent (108) may be provided using a modified metal material. Such materials may be fabricated by, e.g., femtosecond etching lasers for surface modification of a metallic substrate (e.g., blacken metals for absorption at particular wavelengths of light). These materials may be dispersed in a media to absorb fiber light. In another example, infrared dye 1110 (e.g., organic dye-metal complex of the (substituted) aminium chemical family) may be employed.

The tip portion 102 may include material that is biocompatible. The tip is preferably small, e.g., its length d is 5 mm or less, preferably 2 mm or less, and more preferably 1 mm or less. A tip diameter is preferably sub-millimeter, preferably with a same diameter as the optical shape sensing fiber tether. In one embodiment, an interface 106 between fiber 104 and tip portion 102 could be slanted, ridged or otherwise geometrically formed to minimize reflection in case of imperfect refractive index matching. The interface 106 may include a ferrule connection having highly polished and shaped contact surfaces to reduce back-reflections.

In one embodiment, a distal end surface of the tip portion 102 is configured to have a favorable shape S to reflect, defocus or scatter any remaining light. This may include ridges, a slant, or other light scattering features. The shape S can form a complex maze-like structure that wraps upon itself to increase the effective path length traversed by light in the cores while keeping the overall footprint of the tip portion small. The optical shape S and finish of the distal end portion of the tip portion 102 determine the direction of any back reflected light. The present embodiments may simultaneously suppress the reflections from the tip portion 102 of multi-core optical fibers, which may include, e.g., 3 to 7 cores or single mode fibers (SMF).

The tip portion 102 controls a reflection limit. For Fiber Bragg Grating (FBG) optical fibers, an integral reflection over 1 mm is approximately $R_{1\,mm} = 10^{-4}$, where the integral reflection for Rayleigh scattering over the same length is approximately $10^{-6}$. A matching medium (tip portion 102) may have a size on the order of 1 mm or less, so an absorption length $l_{abs}$ should be less than that. This determines the minimum absorption coefficient α and imaginary part of the refractive index k at the interrogation wavelength $\lambda_{vac}$:

$$l_{abs} = \frac{\lambda_{vac}}{4\pi k} = \frac{1}{\alpha'} = \frac{1}{\alpha \ln 10}$$

As an example, realistic values for pure water at 1550 nm are n=1.311 and k=1.35×10⁻⁴, so $l_{abs}$=0.914 mm. The intensity loss due to a double pass through the absorbing tip portion 102 of length d is:

$I = I_0 e^{-2d/l_{abs}}$, where $I_o$ is the initial intensity. The reflection at the fiber/absorber interface 106 due to index mismatch is:

$$R_{fa} = \frac{(n-n_0)^2 + k^2}{(n+n_0)^2 + k^2},$$

where n and k are the real and imaginary part of the refractive index of the tip fiber material.

For a single mode fiber (e.g., SMF28e), the refractive index at 1550 nm is $n_0$=1.468. The reflection at the absorber distal end ($R_{ae}$) depends on any further material, such as tissue, water, or worst case it could be air (n=1), in which case, we have:

$$R_{ae} = \frac{(n-1)^2 + k^2}{(n+1)^2 + k^2}.$$

The curvature or roughness of this interface 106 will also determine any potential reflection of light back into the original guided optical fiber mode. This will introduce an extra factor S that accounts for surface shape of the distal end of tip 102. For example, diffraction at the fiber end (104) will give a diverging beam of width:

$$\tan\theta' = \frac{a'}{z} = \frac{\lambda_{vac}}{\pi n a}.$$

For a single-mode fused silica optical fiber, a numerical aperture is NA=sin θ=n sin θ'=0.14 (e.g., for a Corning™ SMF-28e). The Mode Field Diameter of this fiber is 2a=10.5 micron at 1550 nm. For distance z from the fiber end equal to the absorber length d=1 mm, we can calculate the diameter of the diffracted spot to be 2a'=0.13 mm, that is 154 times the original area, and for a round trip this would potentially reduce the back reflection by an extra factor of 4 so that S=1/600.

From the construction of optical fiber connectors, it is known that their back reflection can be reduced by proper polishing (reduced scattering), in particular at an angle of 8°. This angle happens to correspond to the NA=0.14, but is larger than the internal aperture angle of 5.6°, and hence the reflected light cannot find its way back into the guided mode.

The same optical fiber considered above (Corning™ SMF-28e) has attenuation that is less than 0.4 dB/km, hence $\alpha=0.04$ km$^{-1}$, $l_{abs}=10.86$ km and $k=1.14\times10^{-11}$, with: $I=I_0 10^{-\alpha d}$.

Assuming that interference effects are insignificant, the total reflection at the distal tip would be:
$R_{tot}=\lfloor(R_{fa}+(1-R))_{fa}\rfloor R_{ae}Se^{-2d/l_{abs}}$ where $R_{fa}$ is the reflection at interface 106 and $R_{ae}$ is the reflection from the distal end.

An optimum solution fulfills the condition $n=n_0$, and if we choose S=1 (e.g., the least favorable choice as it is obtained by giving an end facet a radius of curvature equal to the length of the absorber), we find:

$$R_{tot} = \frac{(n_0-1)^2+k^2}{(n_0+1)^2+k^2} + \frac{(2n_0)^2}{(n_0+1)^2+k^2}\frac{k^2}{(2n_0)^2+k^2}e^{-8\pi kd/\lambda_{vac}}$$

From this equation, we can deduce a minimum reflection value ($k_{min}$) given a desired total minimum reflection value $R_{min}$ for a given length of the absorber d. $k_{min}$ is an optimum value for the extinction coefficient k, given a certain length d of the tip, such that the reflection is minimal.

Figure 2:
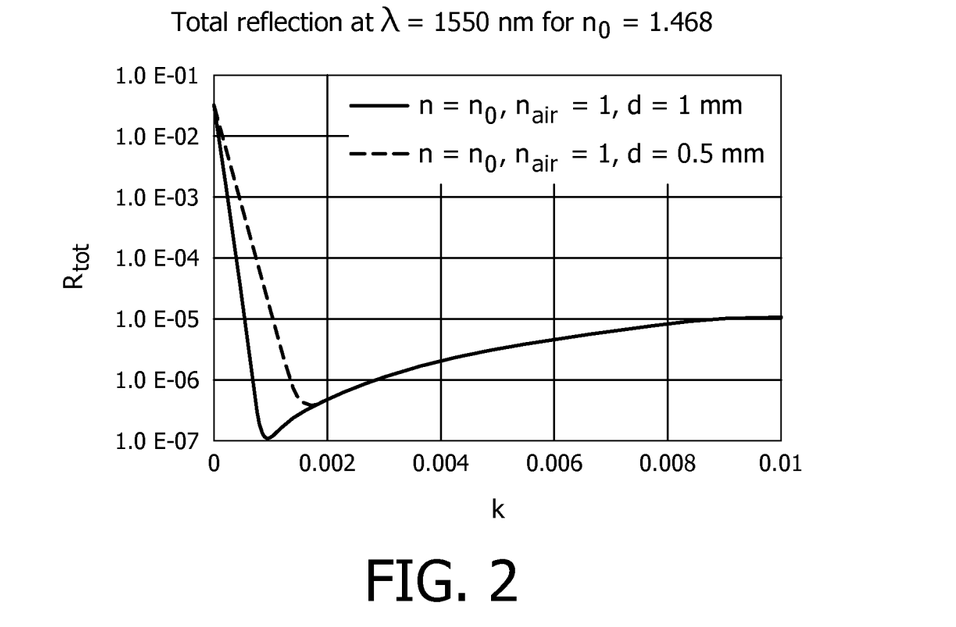
FIG. 2 is a plot of total reflection versus extinction coefficient (k) for a single mode fiber (e.g., SMF28e) at a 1550 nm wavelength and an index of refraction $n_0$ of 1.468 for determining a minimum reflection extinction coefficient ($k_{min}$) in accordance with the present principles.

Referring to FIG. 2, a plot of total reflection versus k for a silica fiber at a 1550 nm wavelength and an index of refraction $n_0$ of 1.468 is shown. For FIG. 2, we find that for a silica fiber at a wavelength of 1550 nm that there is a lower bound to the reflection of $R_{min}=1.12\times10^{-7}$ for $k=0.0009=k_{min}$ if we allow d=1 mm. In accordance with the present principles, one embodiment may employ a highly absorptive dopant diffused into the optical fiber material with $k_{dopant}\gg k_{min}$ and apply the dopant in sufficient concentration in that material. Another embodiment may include providing a material that naturally has $n=n_0$ and $k=k_{min}$ under a given set of conditions.

For example, a tip portion 102 may include graphite nanoparticles in a hydrogel or other fluid solution. In another example, a laser processed metal material may be employed for perfectly absorbing light at specific wavelengths using femtosecond etching lasers for surface modification of a metallic substrate or employing flakes or particles or such processed metal in a matrix material. In yet another embodiment, particular conditions may be determined and a material selected that provides $n=n_0$ and $k=k_{min}$ for interrogation wavelengths.

Figure 3:
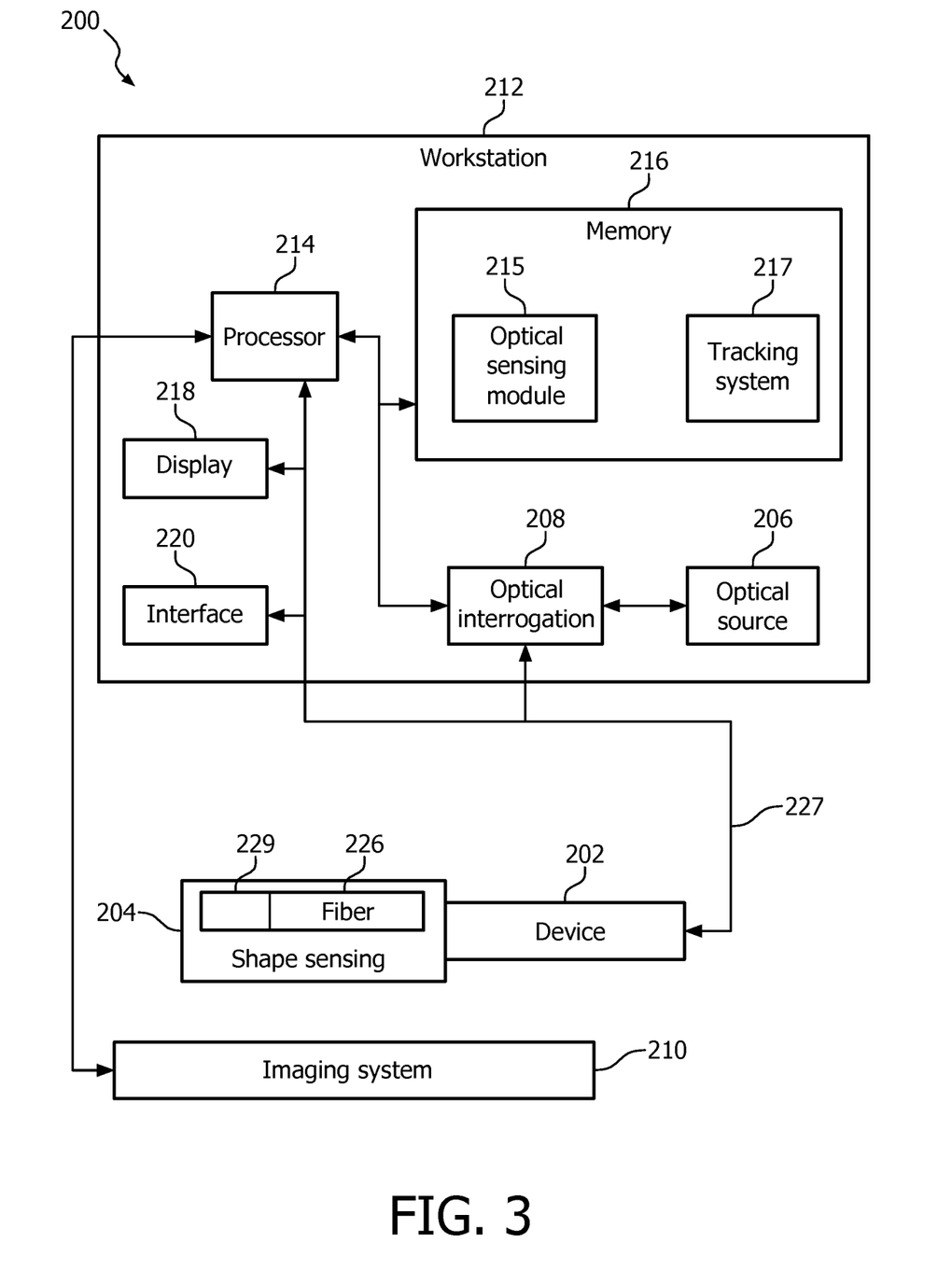
FIG. 3 is a block/flow diagram showing a shape sensing system which employs a tip configuration in accordance with one embodiment.

Referring to FIG. 3, a system 200 for configuring a tip portion 229 and employing a fiber 226 with the tip portion 229 is illustratively shown. System 200 may include a workstation or console 212 from which a procedure is supervised and/or managed. Workstation 212 preferably includes one or more processors 214 and memory 216 for storing programs and applications. Memory 216 may store an optical sensing module 215 configured to interpret optical feedback signals from a shape sensing device or system 204. Optical sensing module 215 is configured to use the optical signal feedback (and any other feedback, e.g., electromagnetic (EM) tracking) to reconstruct deformations, deflections and other changes associated with a medical device or instrument 202 and/or its surrounding region. The medical device 202 may include a catheter, a guidewire, a probe, an endoscope, a robot, an electrode, a filter device, a balloon device, or other medical component, etc.

The shape sensing system 204 on device 202 includes one or more optical fibers 226 which are coupled to the device 202 in a set pattern or patterns. The optical fibers 226 connect to the workstation 212 through cabling 227. The cabling 227 may include fiber optics, electrical connections, other instrumentation, etc., as needed. On a distal end of the optical fibers 226, the tip portion 229 may be attached or applied. The tip portion 229 may include a prefabricated material attached to a distal end of the optical fiber 226. The pre-fabricated material may include a material applied to the tip portion 229, may includes a tip portion attached or spliced to the fiber 226, may include a tip portion dynamically altered using optical feedback to obtain desired properties, etc.

In one embodiment, the prefabricated material of the tip portion 229 may be attached to the distal end portion of the fiber by a splice or other attachment mechanism. The interface between the fiber and the tip portion 229 may be slanted or otherwise geometrically angled to reduce back reflection. The prefabricated material may include light absorbing dopants or dyes as described above. In a particularly useful embodiment, the distal fiber end may be attached to an inside wall of the device 202. In one embodiment, the wall of the device 202 may function as the tip portion 229.

In another embodiment, a material may be applied to the tip portion 229. In this embodiment, a liquid, adhesive or gel may be applied to the distal end of the fiber 226. The liquid or gel may be monitored using the sensing module 215. The liquid or gel may be altered by adding dopants or other materials until desired characteristics are achieved. The material may be permitted to solidify, if needed, to ensure the maintenance of the desired characteristics.

Figure 4:
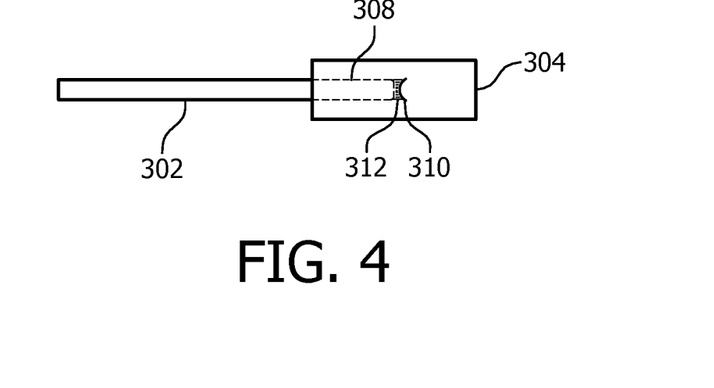
FIG. 4 is another illustrative tip configuration for an optical fiber in accordance with the present principles.

Referring to FIG. 4, another embodiment includes a tip portion 304 which forms an absorption cavity 308. The absorption cavity 308 fits over or is formed over an end portion of an optical fiber 302. A configuration and material of the cavity 308 may be optimized or adjusted dynamically based upon tip reflection measurements or attached based upon use scenarios. The cavity 308 may include some of the following illustrative configurations. In one embodiment, the cavity 308 includes a sleeve that fits over the end portion of the fiber and may include index matching gel 312 in the cavity 308. In another embodiment, the cavity 308 includes a liquid or gel and accepts dopants or particulates. The concentration of the dopants or particulates may be adjusted based upon reflective measurements. The liquid or gel is then preferably solidified. In another embodiment, the cavity 308 may include a ferrule connection 310 with an end portion of the fiber. The ferrule connection 310 selected preferably provides the lowest amount of back-reflection (e.g., polished contact surfaces between the fiber and the tip portion with no air gaps therebetween).

Fiber optic connectors can have several different ferrule shapes or finishes, usually referred to as polishes. The polish on a fiber connector ferrule determines the amount of back reflection. Back reflection is a measure of the light reflected off the polished end of a fiber connector usually measured in negative dB. The ferrule connections may include an air gap, physically contacted surfaces, an angled physical contact interface, index matching gel, etc.

In another embodiment, the tip portion 304 may include multiple absorbing fiber optic cores, one for each of the optical cores within a shape sensing fiber 302. This approach may be more costly and challenging to fabricate due to the need to align the cores between the shape sensing body and tip portions. However, an advantage is that crosstalk between optical cores can be further minimized with such a design.

Referring again to FIG. 3, workstation 212 may include a display 218 for viewing internal images of a subject (patient) if an imaging system 210 is employed. Imaging system 210 may include a magnetic resonance imaging (MRI) system, a fluoroscopy system, a computed tomography (CT) system, etc. Display 218 may also permit a user to interact with the workstation 212 and its components and functions, or any other element within the system 200. This is further facilitated by an interface 220 which may include a keyboard, mouse, a joystick, a haptic device, or any other peripheral or control to permit user feedback from and interaction with the workstation 212.

System 200 may include an EM tracking or similar position or orientation sensing system 217 which may be integrated with the workstation 212 or be a separate system. Workstation 212 includes an optical source 206 to provide optical fibers with light. An optical interrogation unit or module 208 is employed to detect light returning from all fibers. This permits the determination of strains or other parameters, which will be used to interpret the shape, orientation, or other characteristics, sensed by the interventional device 202. The light signals will be employed as feedback to make adjustments to access errors and to calibrate the device 202 or system 200.

Shape sensing device 204 may include one or more fibers 226 with tip portions 229. The tip portions 229 prevent or reduce back reflections to enable shape-sensing down to the distal end of the fiber. The fiber ends will now be well-defined and can be exploited for shape-sensing. Optical interrogation module 208 works with optical sensing module 215 (e.g., shape determination program) to permit a determination of a location and orientation of the tip portion 229 as well as shape of the instrument or device 202. The present principles enable real-time characterization of any elongated instrument based on minimally invasive interventions, in which the shape of the device is needed for improving the accuracy of navigation or targeting.

Figure 5:
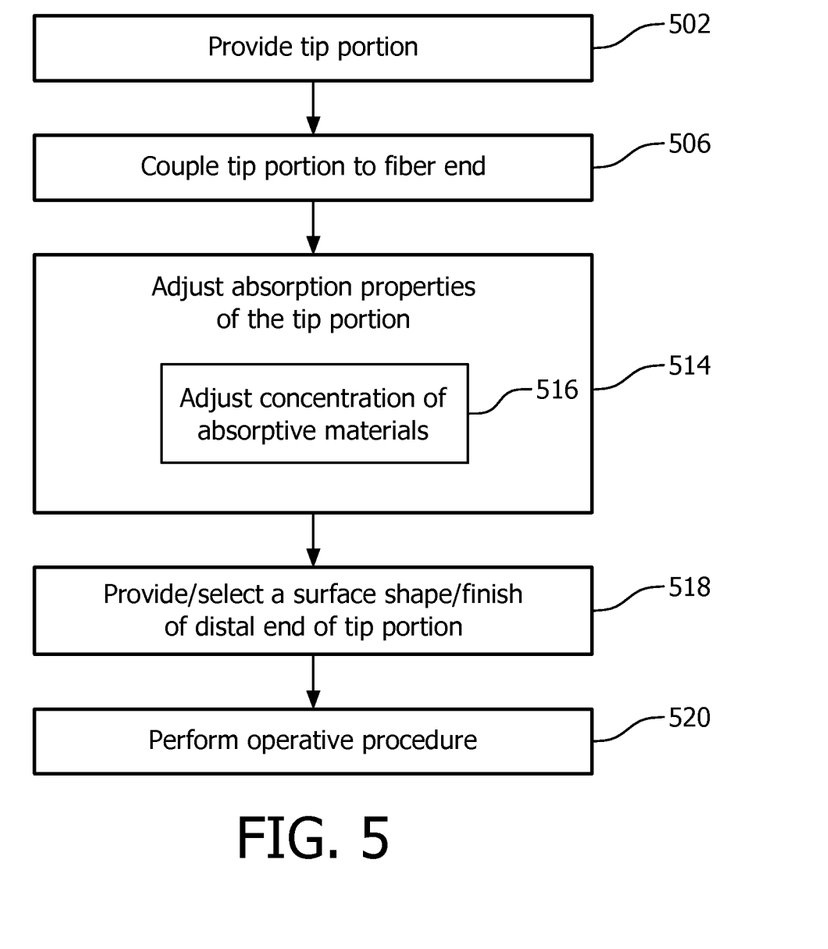
FIG. 5 is a flow diagram showing a method for end-reflection reduction of an optical shape-sensing fiber in accordance with an illustrative embodiment.

Referring to FIG. 5, a method for end-reflection reduction of an optical shape-sensing fiber is illustratively shown. In block 502, a tip portion including an overall length is provided. The overall length is preferably less than about 5 mm.

In block 506, the tip portion is coupled to an end portion of an optical fiber. The fiber may be configured for optical shape-sensing or other applications. The tip portion is refractive index matched to the optical fiber.

In block 514, in one embodiment, the absorption properties of the tip portion are adjusted using back reflections as feedback to provide an absorption length for light traveling in the optical fiber to be less than the length dimension of the tip portion. The tip portion may include a media including light absorbing dopants or particulates. The adjustment of the absorption properties may include adjusting a concentration of dopants or particulates, in block 516.

The light absorbing dopants or particulates may include graphite, nanotubes, buckyballs, a metal complex or particles, cations, anions, a modified metal material fabricated by femtosecond etching lasers for surface modification of a metallic substrate and a dye. The light absorbing dopants or particulates may include a metal having a relative permittivity of about 2 at a plasmon frequency. The light absorbing dopants or particulates may have a minimum reflection extinction coefficient ($k_{min}$) for a given length. The tip portion may include a material with an index of refraction matched to that of the optical fiber and a minimum reflection extinction coefficient ($k_{min}$) for a given length.

In block 518, a distal end shape and/or finish (S) is provided or selected to further reduce back reflections. In block 520, an operative procedure is carried out employing the tip portion to reduce back reflection to further distinguish an end of the optical fiber and/or the end portion of the medical device.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for tip reflection reduction for shape-sensing optical fiber (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A reflection reduction device, comprising:
an optical fiber configured for optical shape-sensing and having an end portion; and
a tip portion coupled to the end portion, the tip portion having a length dimension (d) and being index matched to the optical fiber, the tip portion comprising an absorption length having at least one material on interior and exterior portions of the absorption length that is configured to absorb and scatter light within the length dimension, wherein the absorption length for light traveling in the optical fiber is less than the length dimension.

2. The reflection reduction device as recited in claim 1, wherein the optical fiber and the tip portion share a ferrule connection interface.

3. The reflection reduction device as recited in claim 1, wherein the at least one material on the interior and exterior portions of the absorption length and the tip portion comprises a media having light absorbing dopants or particulates.

4. The reflection reduction device as recited in claim 3, wherein the light absorbing dopants or particulates include a metal having a relative permittivity of about 2 at a plasmon frequency.

5. The reflection reduction device as recited in claim 3, wherein the light absorbing dopants or particulates provide a minimum reflection extinction coefficient (kmin) for a given length dimension.

6. The reflection reduction device as recited in claim 3, wherein the tip portion includes a material with an index of refraction matched to that of the optical fiber and a minimum reflection extinction coefficient (kmin) for a given length dimension.

7. The reflection reduction device as recited in claim 1, wherein the at least one material on the absorption length that is configured to absorb and scatter light is included on a face of a distal end of the tip portion.

8. The reflection reduction device as recited in claim 1, wherein the tip portion further comprises a surface opposite the end portion having a shape comprising a slant that is configured to reduce back reflections.

9. The reflection reduction device as recited in claim 1, wherein the at least one material on the interior and exterior portions of the absorption length comprises tip portion includes a media having light absorbing dopants or particulates.

10. The reflection reduction device as recited in claim 8, wherein the shape is configured to reflect, defocus or scatter any remaining light.

11. A shape sensing system, comprising:
a shape sensing enabled medical device having at least one optical fiber;
a console configured to receive optical signals from the at least one optical fiber and interpret the optical signals to determine a shape of the medical device; and
a tip portion coupled to a distal end portion of the at least one optical fiber, and comprising an absorption length having at least one material on interior and exterior portions of the absorption length that is configured to absorb and scatter light within the length dimension, and a surface (S) opposite the end portion having a shape comprising ridges or a slant that is configured to reduce back reflections.

12. The system as recited in claim 11, wherein the tip portion includes a media having light absorbing dopants or particulates.

13. The system as recited in claim 12, wherein the light absorbing dopants or particulates include a metal having a relative permittivity of about 2 at a plasmon frequency.

14. The system as recited in claim 12, wherein the light absorbing dopants or particulates have a minimum reflection extinction coefficient (kmin) for a given length dimension.

15. The system as recited in claim 12, wherein the tip portion includes a material with an index of refraction matched to that of the optical fiber and a minimum reflection extinction coefficient (kmin) for a given length dimension.

16. A reflection reduction device, comprising:
an optical fiber configured for optical shape-sensing and having an end portion, the optical fiber comprising: a distal end portion of a medical device having shape-sensing capabilities; and the medical device is one of a catheter, a guide wire, an endoscope, a probe, a robot, an electrode, a filter device, or a balloon device; and
a tip portion coupled to the end portion having a length dimension (d) and being index matched to the optical fiber, and an index of refraction matched to that of the optical fiber and a minimum reflection extinction coefficient (kmin) for a given length dimension, the tip portion comprising: an absorption length having at least one material on interior and exterior portions of the absorption length that is configured to absorb and scatter light within the length dimension, wherein the at least one material comprises light absorbing dopants or particulates.

17. The reflection reduction device as recited in claim 16, wherein the optical fiber and the tip portion share a ferrule connection interface.

18. The reflection reduction device as recited in claim 16, wherein the light absorbing dopants or particulates include a metal having a relative permittivity of about 2 at a plasmon frequency.

19. The reflection reduction device as recited in claim 16, wherein the light absorbing dopants or particulates provide a minimum reflection extinction coefficient (kmin) for a given length dimension.

* * * * *